(12) United States Patent
Ma et al.

(10) Patent No.: US 11,873,472 B2
(45) Date of Patent: Jan. 16, 2024

(54) THREE-DIMENSIONAL CULTURE DEVICE AND METHODS FOR DYNAMIC CULTURE OF CELL AGGREGATES

(71) Applicants: FLORIDA STATE UNIVERSITY RESEARCH FOUNDATION, INC., Tallahassee, FL (US); Gary K. Ostrander, Tallahassee, FL (US)

(72) Inventors: Teng Ma, Tallahassee, FL (US); Ang-Chen Tsai, Tallahassee, FL (US); Xuegang Yuan, Tallahassee, FL (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 334 days.

(21) Appl. No.: 17/026,617

(22) Filed: Sep. 21, 2020

(65) Prior Publication Data
US 2021/0009932 A1 Jan. 14, 2021

Related U.S. Application Data

(63) Continuation of application No. 15/809,706, filed on Nov. 10, 2017, now abandoned.

(51) Int. Cl.
*C12M 3/06* (2006.01)
*C12N 5/00* (2006.01)
*C12M 1/12* (2006.01)

(52) U.S. Cl.
CPC ............ *C12M 23/16* (2013.01); *C12M 25/14* (2013.01); *C12M 27/16* (2013.01); *C12N 5/0062* (2013.01);
(Continued)

(58) Field of Classification Search
CPC ..... C12M 23/16; C12M 27/16; C12N 5/0062; C12N 2513/00; C12N 2533/12; C12N 2533/30; C12N 2533/14; C12N 2527/00
See application file for complete search history.

(56) References Cited

U.S. PATENT DOCUMENTS

2003/0235908 A1* 12/2003 Berenson ........... C07K 16/2878
435/372
2016/0282338 A1* 9/2016 Miklas ................... C12M 35/02

OTHER PUBLICATIONS

Bara, J. J. et al. "Concise review: Bone marrow-derived mesenchymal stem cells change phenotype following in vitro culture: Implications for basic research and the clinic," *Stem Cells*, 2014, 32:1713-1723.

(Continued)

*Primary Examiner* — Michael L Hobbs
(74) *Attorney, Agent, or Firm* — SALIWANCHIK, LLOYD & EISENSCHENK

(57) ABSTRACT

The subject invention concerns materials and methods for culture of cell aggregates. The subject invention utilizes three-dimensional (3-D) inserts comprising micro-channels having selected dimensions. The inserts are provided in or on tissue culture plates that can be supported on a programmable rocking platform/station, thereby providing for a hydrodynamic environment that promotes 3-D aggregation of cells cultured on the plates. The supporting rocker is programmed to provide motion that generates hydrodynamic conditions that support 3-D cell aggregation and long-term culture. The subject invention also concerns an apparatus comprising a tissue culture vessel that comprises a 3-D insert of the present invention, and a programmable rocking platform/station that can provide motion to the vessel provided thereon, thereby generating hydrodynamic conditions and wave motion that support 3-D cell aggregation and cell culture. The subject invention also concerns methods for growing 3-D aggregates of cells.

16 Claims, 8 Drawing Sheets
(1 of 8 Drawing Sheet(s) Filed in Color)

(52) U.S. Cl.
CPC ...... *C12N 2513/00* (2013.01); *C12N 2527/00* (2013.01); *C12N 2533/12* (2013.01); *C12N 2533/14* (2013.01); *C12N 2533/30* (2013.01)

(56) References Cited

OTHER PUBLICATIONS

Wang, W. et al. "3D spheroid culture system on micropatterned substrates for improved differentiation efficiency of multipotent mesenchymal stem cells," *Biomaterials*, 2009, 30:2705-2715.

Potapova, I. A. et al. "Culturing of human mesenchymal stem cells as three-dimensional aggregates induces functional expression of CXCR4 that regulates adhesion to endothelial cells," *J. Biol. Chem.*, 2008, 283:13100-13107.

Bhang, S. H. et al. "Transplantation of cord blood mesenchymal stem cells as spheroids enhances vascularization," *Tissue Eng. Part A*, 2012, 18:2138-2147.

Bartosh, T. J. et al. "Aggregation of human mesenchymal stromal cells (MSCs) into 3D spheroids enhances their antiinflammatory properties," *Proc. Natl. Acad. Sci. U.S.A.*, 2010, 107:13724-13729.

Bhang, S. H. et al. "Angiogenesis in ischemic tissue produced by spheroid grafting of human adipose-derived stromal cells," *Biomaterials*, 2011, 32:2734-2747.

Katagiri, H. et al. "Transplantation of aggregates of synovial mesenchymal stem cells regenerates meniscus more effectively in a rat massive meniscal defect," *Biochem. Biophys. Res. Commun.*, 2013, 435:603-609.

Suzuki, S. et al. "Properties and usefulness of aggregates of synovial mesenchymal stem cells as a source for cartilage regeneration," *Arthritis Res. Ther.*, 2012, 14:R136.

Lee, E. J. et al. "Spherical bullet formation via E-cadherin promotes therapeutic potency of mesenchymal stem cells derived from human umbilical cord blood for myocardial infarction," *Mol. Ther.*, 2012, 20:1424-1433.

Johnstone, B. et al. "In vitro chondrogenesis of bone marrow-derived mesenchymal progenitor cells," *Exp. Cell Res.* 1998, 238:265-272.

Sart, S. et al. "Three-dimensional aggregates of mesenchymal stem cells: Cellular mechanisms, biological properties, and applications," *Tissue Eng. Part B*, 2014, 23:365-380.

Baraniak, P. R. et al. "Scaffold-free culture of mesenchymal stem cell spheroids in suspension preserves multilineage potential," *Cell Tissue Res.*, 2012, 347:701-711.

Kim, J. et al. "Endogenous extracellular matrices enhance human mesenchymal stem cell aggregate formation and survival," *Biotechnol. Progr.*, 2013, 29:441-451.

Occhetta, P. et al. "High-throughput microfluidic platform for 3D cultures of mesenchymal stem cells, towards engineering developmental processes," *Sci. Rep.*, 2015, 5:10288.

Toh, Y.-C. et al. "A novel 3D mammalian cell perfusion-culture system in microfluidic channels," *Lab Chip*, 2007, 7:302-309.

Torisawa, Y.-S. et al. "Efficient formation of uniform-sized embryoid bodies using a compartmentalized microchannel device," *Lab Chip*, 2007, 7:770-776.

Chan, H. F. et al. "Rapid formation of multicellular spheroids in double-emulsion droplets with controllable microenvironment," *Sci. Rep.*, 2013, 3:3462.

\* cited by examiner

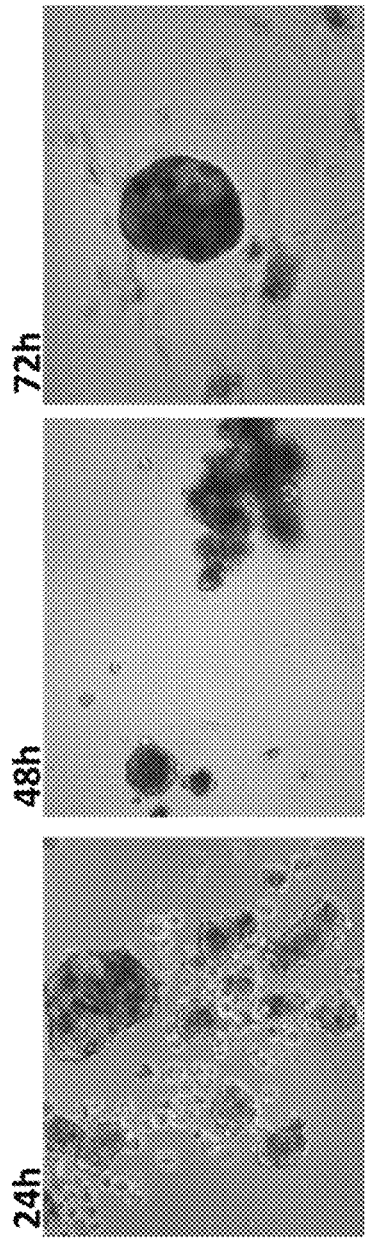
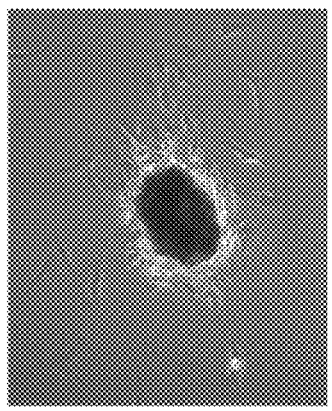
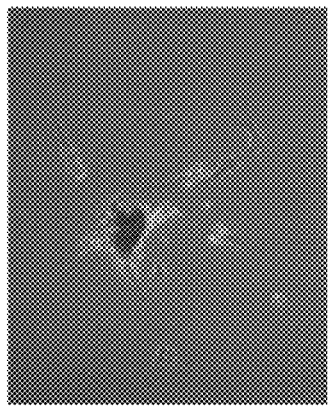
FIG. 3A  FIG. 3B  FIG. 3C
Replate for 24h:
FIG. 3D  FIG. 3E 24h
48h
50 k cells
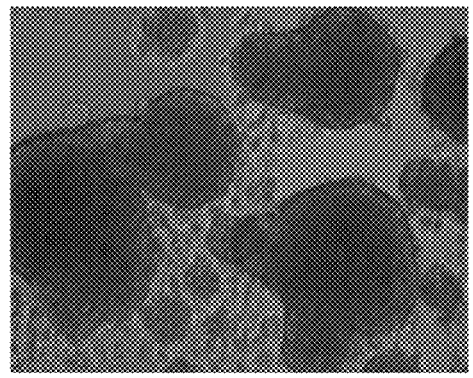
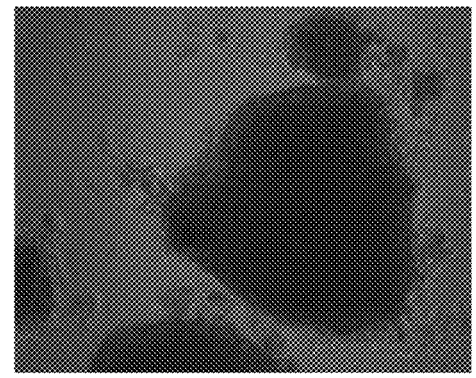
FIG. 4A
FIG. 4B
24h
48h
100 k cells
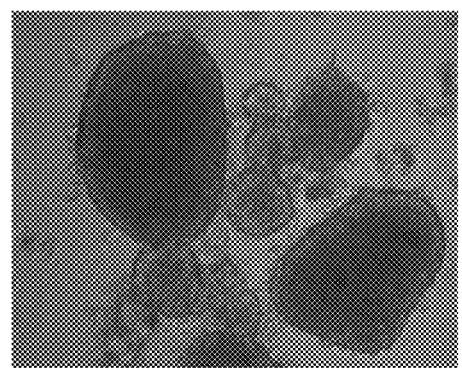
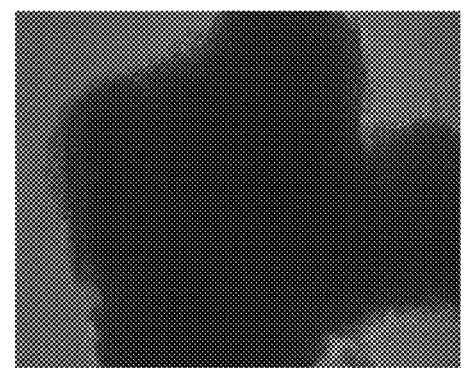
FIG. 4C
FIG. 4D

10 k cells 20 k cells

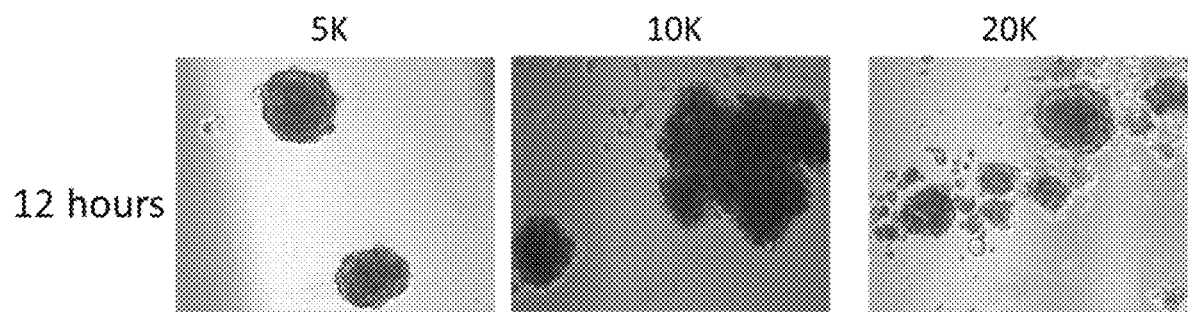
FIG. 6A  FIG. 6B  FIG. 6C
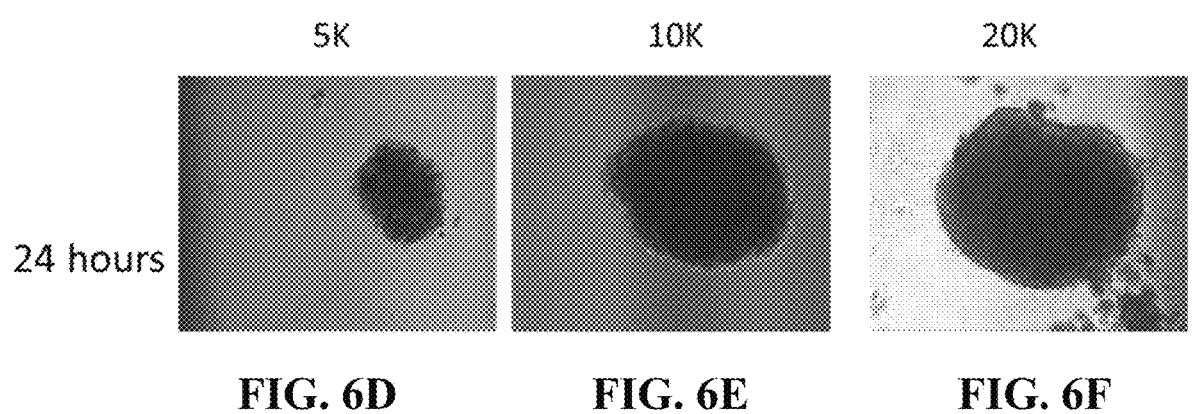
FIG. 6D  FIG. 6E  FIG. 6F

6h
12h
24h
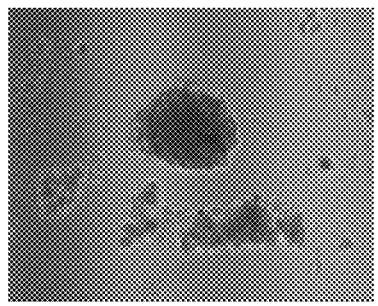 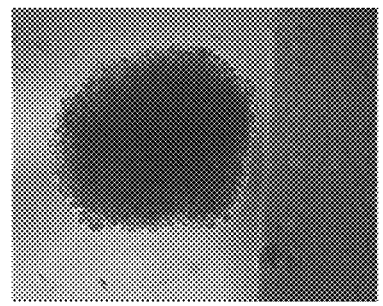 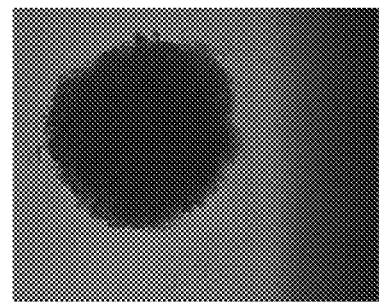
FIG. 7A          FIG. 7B          FIG. 7C
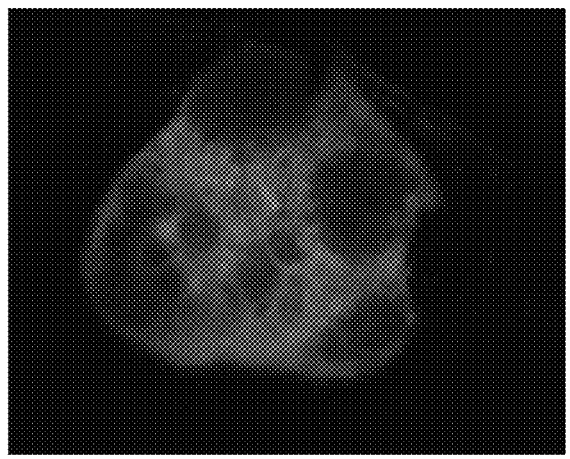 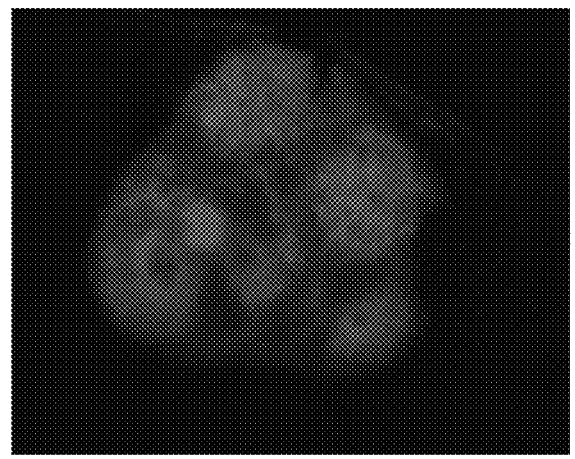
FIG. 8A          FIG. 8B

THREE-DIMENSIONAL CULTURE DEVICE AND METHODS FOR DYNAMIC CULTURE OF CELL AGGREGATES

CROSS-REFERENCE TO RELATED APPLICATION

The present application is a continuation of U.S. application Ser. No. 15/809,706, filed Nov. 10, 2017, now abandoned, which is hereby incorporated by reference herein in its entirety, including any figures, tables, nucleic acid sequences, amino acid sequences, or drawings.

BACKGROUND OF THE INVENTION

Human mesenchymal stem cells (hMSCs) are primary candidates in cell therapy and tissue engineering and are tested in clinical trials for a wide range of diseases. In bone marrow, hMSCs occupy an anatomically distinct niche environment with close association with microvasculature. Removal of hMSC from the specialized in vivo niche for in vitro expansion in an artificial culture environment induces progressive changes in hMSC properties that diminish their therapeutic potential, a significant barrier impeding their clinical translation [1]. Recent studies show that hMSC have innate ability to self-assemble into three-dimensional (3-D) aggregates, enhancing their regenerative properties with higher multi-lineage potential [2], increased migration ability [3], up-regulation of antiinflammatory and angiogenic growth factors [4, 5], and improved resistance to ischemic stress post-transplantation [6]. While short-term aggregation has been used as a pretreatment for hMSC functional enhancement, direct transplantation of MSC aggregates has been shown to effectively improve MSC therapeutic benefits in preclinical models including cartilage defect [7, 8], hindlimb ischemia [4], and myocardial infarction [9]. Given the broad enhancement of hMSC property via 3-D aggregation, there is growing interest in the development of novel platform for the scalable production of hMSC aggregates.

As anchorage-dependent cells, hMSCs are conventionally cultured as monolayers and their aggregation in vitro requires close cell-cell contact under physical forces such as centrifugation or spatial confinement. The earliest hMSC aggregate culture was developed in chondrogenic differentiation, in which hMSCs were pelleted into large aggregates under centrifugation force [10]. In the absence of external forces, hMSC can also spontaneously assemble into 3-D aggregates when in close contact in spatially confined spaces if the cell-cell binding force exceeds the cell-substrate adhesion force to allow cell-cell adhesion and compaction [11]. To date, a variety of laboratory methods have been used for the production of hMSC aggregates, including hanging drop, centrifugation, low adhesion surface treatment, and thermal lifting [5, 12, 13]. Advanced microfabrication technologies such as aligned microchambers [14], arrayed micropillars [15], semi-porous membranes [16], and two-phase emulsive droplets [17] have also been developed for laboratory scale production of hMSC aggregates. However, these methods are predominantly used in laboratory scale aggregate production and have limited scalability and/or poor control of aggregate size.

BRIEF SUMMARY OF THE INVENTION

The subject invention concerns materials and methods for culture of cell aggregates. The subject invention utilizes three-dimensional (3-D) inserts comprising micro-channels having selected dimensions. The inserts are provided in or on tissue culture plates or vessels that can be supported on a programmable rocking platform/station, thereby providing for a hydrodynamic environment that promotes 3-D aggregation of cells cultured on the plates or vessels. In one embodiment, one or more micro-channels are provided in a 3-D insert that can be provided in or placed within the tissue culture plate or vessel. Cells are placed in the micro-channels of the inserts in the tissue culture plates or vessels that comprise a suitable cell growth medium for the particular type of cell. The supporting rocker is programmed to provide motion that generates hydrodynamic conditions that support 3-D cell aggregation and long-term culture. Aggregated cells can be harvested and isolated from the micro-channels of the 3-D inserts in the tissue culture plate or vessel at suitable times. Harvested cells or aggregates can optionally be reseeded back into fresh tissue culture media.

The subject invention also concerns an apparatus comprising a tissue culture plate or vessel that comprises a 3-D insert of the present invention, and a programmable rocking platform/station that can provide motion to the vessel provided thereon, thereby generating hydrodynamic conditions and wave motion that support 3-D cell aggregation and cell culture.

The subject invention also concerns methods for growing 3-D aggregates of cells. Methods of the invention comprise culturing cells in a micro-channel of a 3-D insert of the invention provided in or as part of a tissue culture plate or vessel or the well of a tissue culture vessel.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIG. 3A-3E. FIGS. 3A-3C show cell aggregates (5K per micro-channel) from 24, 48, and 72 hours of culture in a 3-D insert of the present invention. FIGS. 3D and 3E show aggregates re-plated on standard tissue culture surface for re-adhesion.

FIGS. 4A-4D show cell aggregates from 24 and 48 hours of culture in a 3-D insert of the present invention, with 50 k and 100 k cells per micro-channel.

FIGS. 6A-6F show cell aggregates from 12 to 24 hours of culture in a 3-D insert of the present invention with gradient cell seeding number (5 k, 10 k, and 20 k of cells per micro-channel).

FIGS. 7A-7C show cell aggregates dynamics from 6 to 24 hours of culture in a 3-D insert of the present invention at seeding density of 20 k cells.

FIGS. 8A and 8B show cell aggregates by successive addition of cells labeled with different colors at different culture time.

DETAILED DESCRIPTION OF THE INVENTION

Figure 1A:
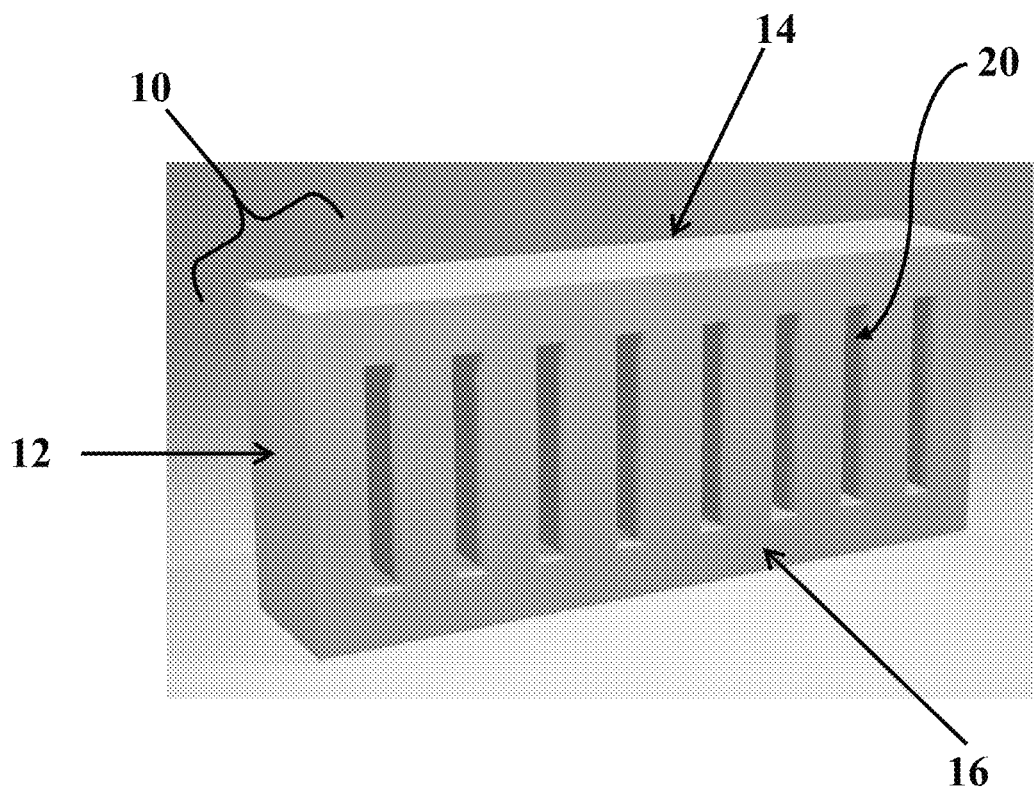
FIGS. 1A-1E are drawings of examples of 3-D inserts of the present invention.
Figure 1B:
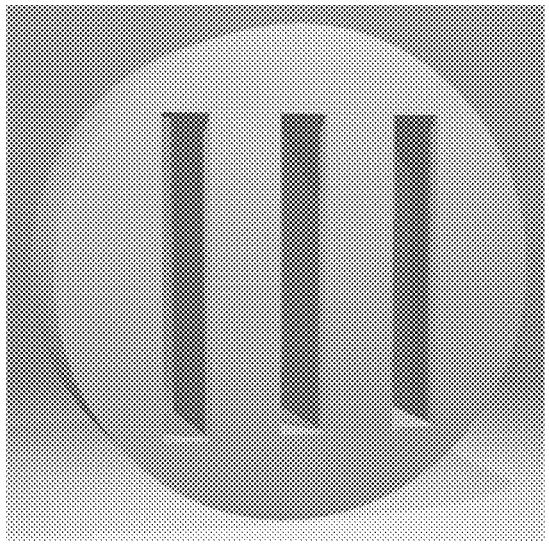
Figure 1C:
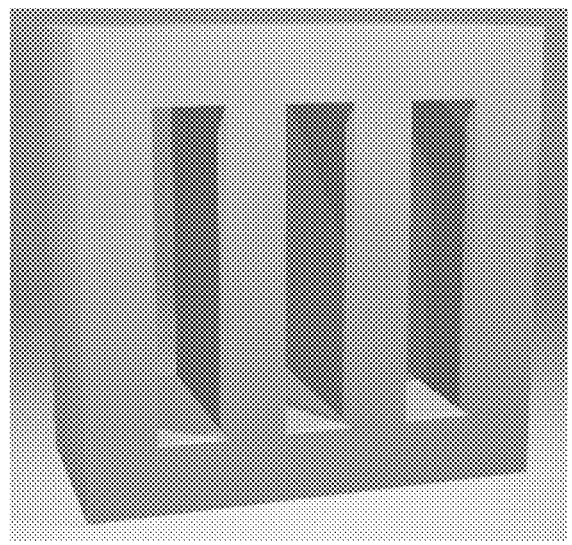
Figure 1D:
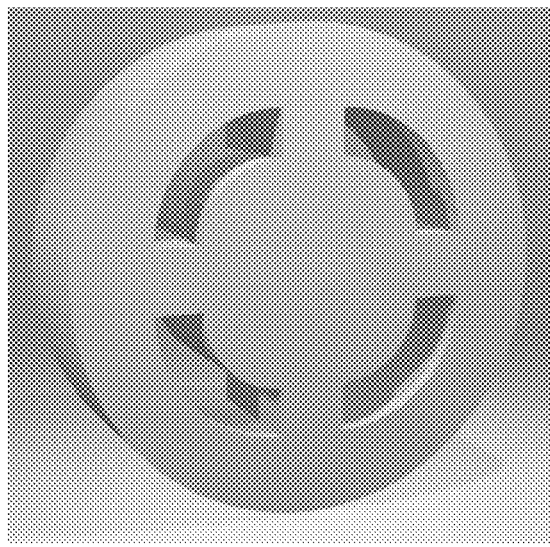
Figure 1E:
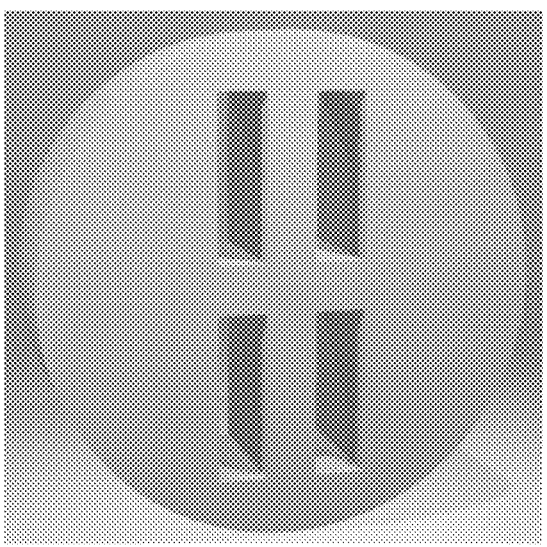
Figure 2A:
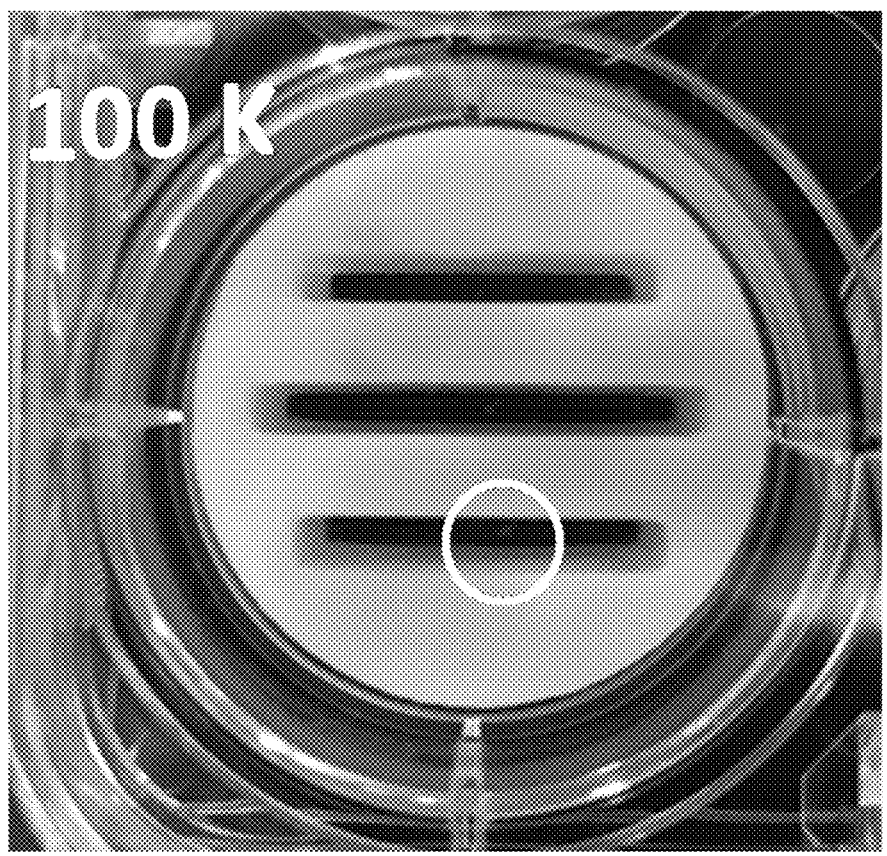
FIGS. 2A and 2B show images of the 3D printed blocks with micro-channels in 6-well plates, seeded with 100 k cells (FIG. 2A) or 50 k cells (FIG. 2B) per micro-channel for 2 days culture. The circles show cell aggregates in a micro-channel.
Figure 2B:
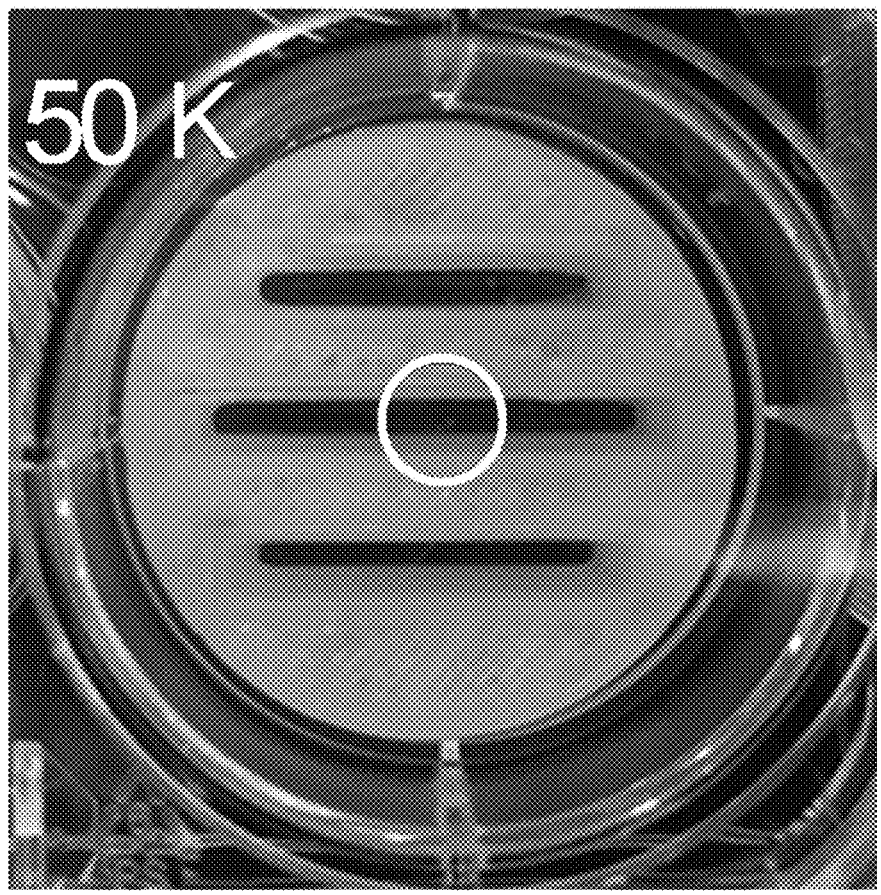
Figures 5A, 5B:
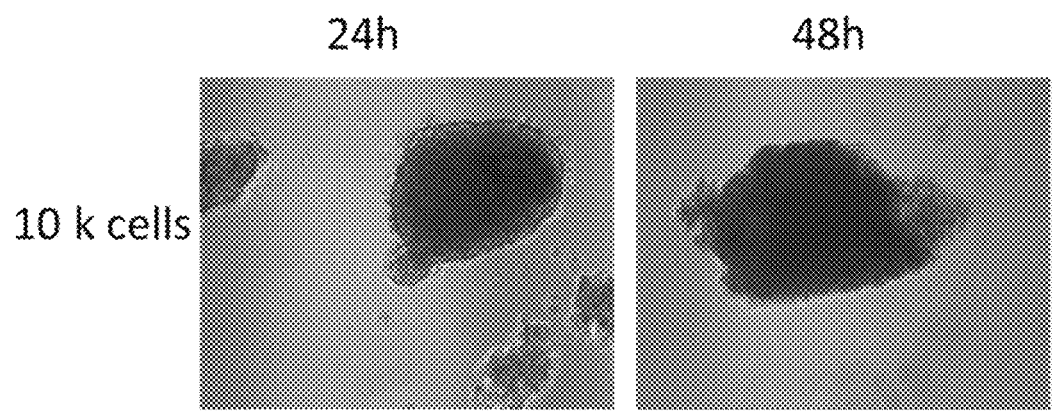
FIGS. 5A-5D show cell aggregates from 24 and 48 hours of culture in a 3-D insert of the present invention with 10 k and 20 k cells per micro-channel.
Figures 5C, 5D:
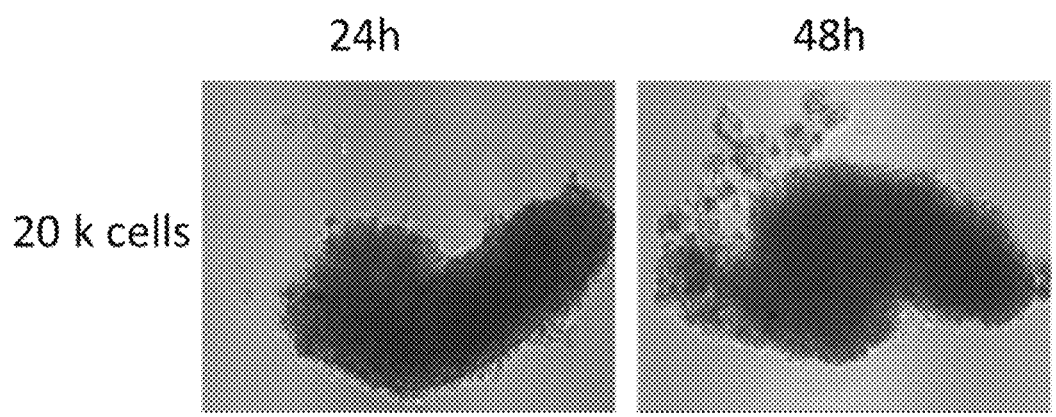

The subject invention concerns materials and methods for producing and culturing cell aggregates. The subject invention utilizes three-dimensional (3-D) inserts for use to create an adjustable confined spatial channel in tissue culture plates or vessels or on a tissue culture surface, the inserts comprising one or more micro-channels and having designed dimensions. Tissue culture plates or vessels with the designed 3-D inserts can be used in conjunction with a programmable rocking platform/station, thereby providing a hydrodynamic environment that promotes 3-D aggregation of cells cultured in the vessels. The 3-D insert can be removable and detachable from the tissue culture plate or vessel and reused for further experiment, or it can be permanently attached to the plate or vessel. The base of the 3-D insert sits on the floor of the cell culture space of the culture plate or vessel, e.g., on the floor of a well of the culture vessel. The 3-D insert can be provided in any suitable size and shape to fit within a culture plate or vessel or the well of a culture vessel. For example, the 3-D insert can be round (cylindrical), square (cube), rectangular (rectangular prism), triangular (triangular prism), pentagonal, hexagonal, heptagonal, octagonal, nonagonal, or decagonal in shape. Examples of round, square, and rectangular 3-D inserts of the invention are shown in FIGS. 1 and 2. FIG. 2 shows 3-D printed inserts with micro-channels built in 6-well tissue culture plates. The 3-D insert can be composed of any suitable material that is compatible with cell culture including, for example, plastic (polystyrene, polypropylene, polycarbonate, etc.), glass, ceramic, metal, metal alloys, composites, etc. In one embodiment, the 3-D insert is produced by 3-D printing. The dimension and design of 3-D inserts can be plotted using SOLIDWORKS software and create the molds for 3-D printing. The 3-D insert can also be produced using any other method suitable for the material to be utilized (e.g., injection molding, vacuum forming, computer numeric control (CNC) machining and milling, etc.).

As shown in FIGS. 1A-1E, a 3-D insert 10 of the invention can comprise one or more open micro-channels 20 within one 3-D insert. In various embodiments, the 3-D insert comprises a side wall or sides (12), a generally flat base surface (14) and an upper surface (16). In one embodiment, an insert comprises from one to ten micro-channels. The micro-channels can be linear straight (as in FIGS. 1A-1C and 1E) or curved (as in FIG. 1D) or any other design, such as zig-zagged or irregular. In one embodiment, the micro-channel dimensions have a width of about 1 mm to 5 mm, a length of about 20 mm to 60 mm, and a height of about 5 mm to 15 mm (the height is generally the same as the height of a side wall of the 3-D insert). In an exemplified embodiment, the channel dimensions are about 3 mm width by about 20 to 40 mm length by about 10 mm height. The dimensions of micro-channels can also vary within a single 3-D insert, e.g., the length of one channel can be longer or shorter than the length of other channels within an insert (see, for example, FIGS. 2A-2B). In one embodiment, one or more surfaces of the 3-D insert and/or the tissue culture vessel can be coated with or made from a material that inhibits adherence of cells to the surface (e.g., ultra-low attachment (ULA) tissue culture plates (Corning, Corning, NY)).

Cells are placed in the micro-channels of a 3-D insert that is present in the tissue culture plate or vessel wherein the vessel and/or micro-channels comprises a suitable cell culture medium for the particular cell type being cultured. The tissue culture plate or vessel with 3-D insert and cells can be provided or placed on a programmable rocking platform/station. The supporting rocker platform/station is programmed to provide motion that generates hydrodynamic conditions in the tissue culture plate or vessel that support 3-D cell aggregation and long-term culture. Examples of supporting rockers that can be utilized are known in the art, e.g., the WAVE Rocker by GE Healthcare Life Sciences. In one embodiment, the rocking frequency of the rocking platform/station can be several rocks per minute (rpm), e.g., 2 to 40 rpm. In a specific embodiment, the rocking frequency is about 5 rocks per minute (rpm). In one embodiment, the rocking angle of the rocking platform/station can be from about 1 to about 25 degrees. In exemplified embodiments, the rocking angle is about 15 to about 20 degrees. Following culture in the present invention, aggregated cells can be harvested and isolated from the micro-channels of the 3-D insert in the tissue culture plate or vessel at suitable times. Harvested cell aggregates can optionally be reseeded back into fresh tissue culture media.

The subject invention also concerns an apparatus comprising a tissue culture plate or vessel that comprises a 3-D insert of the present invention, and a programmable rocking platform/station that can provide controlled motion in the culture channel, thereby generating hydrodynamic conditions and wave motion that support 3-D cell aggregation and cell culture.

The subject invention also concerns methods for growing 3-D aggregates of cells. Methods of the invention comprise culturing cells in a micro-channel of a 3-D insert of the invention provided in or as part of a tissue culture plate or vessel or the well of a tissue culture vessel. In one embodiment, cells are added to a micro-channel in a suitable cell culture medium for the type of cell being utilized. In one embodiment, the culture medium can comprise minimum essential medium-alpha ($\alpha$-MEM), penicillin, streptomycin, and/or fetal bovine serum. The cells can be any cell for which culture and growth, and preferably aggregation, is desired. The cells can be, for example, from established cell lines, or cells taken from tissue of an animal. The cells can be human cells or cells from other mammals. In one embodiment, the cells are stem cells, such as mesenchymal stem cells (MSC). MSC can be derived from any suitable tissue, such as bone marrow. In a specific embodiment, the cells are human stem cells. In a more specific embodiment, the cells are human MSC. Stem cells can be obtained, for example, from bone marrow and/or adipose tissue of a human or other mammal. Other cells for which aggregate growth and production is desired can also be cultured using the present invention. In one embodiment, one or more surfaces of the 3-D insert and/or tissue culture plate or vessel can be coated or made from a material that inhibits adherence or attachment of cells to the surface. In one embodiment, the culture plate or vessel containing the 3-D insert is subjected to a rocking condition that generates hydrodynamic conditions that support 3-D cell aggregation and long-term culture. Examples of supporting rockers that can be utilized are known in the art, e.g., the WAVE Rocker by GE Healthcare Life Sciences. In one embodiment, the rocking frequency can be several rpm. In an exemplified embodiment, the rocking frequency is about 5 rpm. In one embodiment, the rocking angle can be from about 1 to 20 degrees. In an exemplified embodiment, the rocking angle is about 15 to about 20 degrees. The temperature, air, $O_2$ and $CO_2$ levels, and other cell culture parameters can be selected based on the cells to be cultured and grown. In one embodiment, the tissue culture plate or vessel on the rocking platform is provided in a humidified environment at about 37° C. and about 5% $CO_2$. Aggregated cells can be harvested and isolated from the micro-channels of the 3-D insert in the tissue culture plate or vessel at any suitable time after the initiation of cell culture in the 3-D insert, e.g., at 18 hours, or at 24 hours, or 48 hours, or 72 hours, or 96 hours, or 120 hours. Harvested cells or aggregates can optionally be reseeded back into fresh tissue culture media.

The subject invention also concerns cells and aggregates thereof grown using a 3-D insert and the methods of the invention.

Materials and Methods

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

A 3-D insert built in a 100 mm diameter non-adherent culture dish (Corning, Corning, NY) was used to culture human bone marrow-derived mesenchymal stem cells. Dimensions of the micro-channels were 3 mm width by 40 mm length by 10 mm height. 50,000 cells were seeded in each microchannel. Final volume of culture medium was adjusted to 400 uL. The culture dish was placed on a programmed rocking platform and cultured for 3 days with the setting at 5 rpm and 20° tilt. FIGS. 3A-3C shows cell aggregates at 24 hours, 48 hours, and 72 hours of culture. Aggregates were collected and replated on standard tissue culture plates for further culture (see FIGS. 3D and 3E).

Example 2

Round 3-D inserts (having three micro-channels of 3 mm width by 20 mm length or 25 mm length by 10 mm height) or square 3-D inserts (having three micro-channels of 15 mm length) were seeded with 50,000 or 100,000 P6 human bone marrow-derived mesenchymal stem cells per channel in 200 μl of culture media in a tissue culture dish on a rocking platform. Rocking frequency was 5 rpm and 15° tilt. Cells were cultured for two days. FIGS. 4A-4D show cell aggregates at 24 and 48 hours.

Example 3

Round 3-D inserts (having three micro-channels of 3 mm width by 20 mm length by 10 mm height) were seeded with 10,000 or 20,000 P7 human bone marrow-derived mesenchymal stem cells per channel in a tissue culture dish on a rocking platform. Final media volume was adjusted to 200 uL. Rocking frequency was 5 rpm and 15° tilt. FIGS. 5A-5D show the cell aggregates generated at 24 and 48 hours of culture.

Example 4

Round 3-D inserts (having three micro-channels of 3 mm width by 20 mm length by 10 mm height) were seeded with 5,000, or 10,000, or 20,000 P6 human bone marrow-derived mesenchymal stem cells per channel in 200 μl of culture media in a tissue culture dish on a rocking platform. Rocking frequency was 5 rpm and 15° tilt. FIGS. 6A-6F show cell aggregates with different cell seeding density at 12 and 24 hours of cell culture.

Example 5

Round 3-D inserts (having three micro-channels of 3 mm width by 20 mm length by 10 mm height) were seeded with 10,000 P6 human bone marrow-derived mesenchymal stem cells per channel in 200 μl of culture media in a tissue culture dish on a rocking platform. Rocking frequency was 5 rpm and 15° tilt. FIGS. 7A-7C show cell aggregates dynamics with different time points of 6, 12 and 24 hours of cell culture.

Example 6

Round 3-D inserts (having three micro-channels of 3 mm width by 20 mm length by 10 mm height) were seeded with 10,000 P6 cells human bone marrow-derived mesenchymal stem cells (labeled with cell tracker red) per channel in 200 μl of culture media in a tissue culture dish on a rocking platform. Rocking frequency was 5 rpm and 15° tilt. After one-day culture, another 10,000 cells (labeled with cell tracker green) were added to the same channel and cultured for another day. FIGS. 8A and 8B show cell aggregates with two different colors after 2 days of cell culture.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

[1] Bara, J. J., Richards, R. G., Alini, M., Stoddart, M. J., Concise review: Bone marrow-derived mesenchymal stem cells change phenotype following in vitro culture: Implications for basic research and the clinic. *Stem Cells* 2014, 32, 1713-1723.

[2] Wang, W., Itaka, K., Ohba, S., Nishiyama, N. et al., 3D spheroid culture system on micropatterned substrates for improved differentiation efficiency of multipotent mesenchymal stem cells. *Biomaterials* 2009, 30, 2705-2715.

[3] Potapova, I. A., Brink, P. R., Cohen, I. S., Doronin, S. V., Culturing of human mesenchymal stem cells as three-dimensional aggregates induces functional expression of CXCR4 that regulates adhesion to endothelial cells. *J. Biol. Chem.* 2008, 283, 13100-13107.

[4] Bhang, S. H., Lee, S., Shin, J.-Y., Lee, T.-J., Kim, B.-S., Transplantation of cord blood mesenchymal stem cells as spheroids enhances vascularization. *Tissue Eng. Part A* 2012, 18, 2138-2147.

[5] Bartosh, T. J., Ylostalo, J. H., Mohammadipoor, A., Bazhanov, N. et al., Aggregation of human mesenchymal stromal cells (MSCs) into 3D spheroids enhances their antiinflammatory properties. *Proc. Natl. Acad. Sci. U.S.A.* 2010, 107, 13724-13729.

[6] Bhang, S. H., Cho, S.-W., La, W.-G., Lee, T.-J. et al., Angiogenesis in ischemic tissue produced by spheroid grafting of human adipose-derived stromal cells. *Biomaterials* 2011, 32, 2734-2747.

[7] Katagiri, H., Muneta, T., Tsuji, K., Horie, M. et al., Transplantation of aggregates of synovial mesenchymal stem cells regenerates meniscus more effectively in a rat massive meniscal defect. *Biochem. Biophys. Res. Commun.* 2013, 435, 603-609.

[8] Suzuki, S., Muneta, T., Tsuji, K., Ichinose, S. et al., Properties and usefulness of aggregates of synovial mesenchymal stem cells as a source for cartilage regeneration. *Arthritis Res. Ther.* 2012, 14, R136.

[9] Lee, E. J., Park, S. J., Kang, S. K., Kim, G.-H. et al., Spherical bullet formation via E-cadherin promotes therapeutic potency of mesenchymal stem cells derived from human umbilical cord blood for myocardial infarction. *Mol. Ther.* 2012, 20, 1424-1433.

[10] Johnstone, B., Hering, T. M., Caplan, A. I., Goldberg, V. M., Yoo, J. U., In vitro chondrogenesis of bone marrow-derived mesenchymal progenitor cells. *Exp. Cell Res.* 1998, 238, 265-272.

[11] Sart, S., Tsai, A.-C., Li, Y., Ma, T., Three-dimensional aggregates of mesenchymal stem cells: Cellular mechanisms, biological properties, and applications. *Tissue Eng. Part B* 2014, 20, 365-380.

[12] Baraniak, P. R., McDevitt, T. C., Scaffold-free culture of mesenchymal stem cell spheroids in suspension preserves multilineage potential. *Cell Tissue Res.* 2012, 347, 701-711.

[13] Kim, J., Ma, T., Endogenous extracellular matrices enhance human mesenchymal stem cell aggregate formation and survival. *Biotechnol. Progr.* 2013, 29, 441-451.

[14] Occhetta, P., Centola, M., Tonnarelli, B., Redaelli, A. et al., High-throughput microfluidic platform for 3D cultures of mesenchymal stem cells, towards engineering developmental processes. *Sci. Rep.* 2015, 5, 10288.

[15] Toh, Y.-C., Zhang, C., Zhang, J., Khong, Y. M. et al., A novel 3D mammalian cell perfusion-culture system in microfluidic channels. *Lab Chip* 2007, 7, 302-309.

[16] Torisawa, Y.-s., Chueh, B.-h., Huh, D., Ramamurthy, P. et al., Efficient formation of uniform-sized embryoid bodies using a compartmentalized microchannel device. *Lab Chip* 2007, 7, 770-776.

[17] Chan, H. F., Zhang, Y., Ho, Y.-P., Chiu, Y.-L. et al., Rapid formation of multicellular spheroids in double-emulsion droplets with controllable microenvironment. *Sci. Rep.* 2013, 3, 3462.

What is claimed is:

1. A method for growing cells into aggregates of cells comprising culturing a cell in a micro-channel of a 3-D tissue culture insert provided in a tissue culture vessel, wherein said tissue culture vessel comprises one or more 3-D tissue culture inserts comprising one or more micro-channels that provide for a confined space for cells that are cultured in said one or more micro-channels and suitable culture media for culturing said cell, wherein said one or more micro-channels have a width of about 1 mm to about 5 mm, a length of about 20 mm to about 60 mm, and a height of about 5 mm to about 15 mm.

2. The method according to claim 1, wherein the 3-D tissue insert fits into a well of a tissue culture vessel.

3. The method according to claim 1, wherein said cell is a mammalian cell or a human cell.

4. The method according to claim 1, wherein said cell is a stem cell.

5. The method according to claim 4, wherein said stem cell is a mesenchymal stem cell.

6. The method according to claim 1, wherein one or more surfaces of said one or more 3-D tissue culture insert is coated with or composed of a material that inhibits or prevents adherence or attachment of a cell to said one or more surfaces.

7. The method according to claim 1, wherein the method further comprises rocking said tissue culture vessel at a frequency to generate hydrodynamic conditions to support cell aggregation.

8. The method according to claim 7, wherein said rocking is at a frequency of about 1 to 5 rocks per minute.

9. The method according to claim 7, wherein said rocking is at a rocking angle of about 15 to about 20 degrees.

10. The method according to claim 1, wherein the method further comprises harvesting said cell aggregates after about 18 to 120 hours of culturing said cell in said micro-channel.

11. The method according to claim 10, wherein said harvested cells are seeded back into culture media for further culturing.

12. The method according to claim 1, wherein said one or more 3-D tissue culture insert is composed of a plastic, glass, ceramic, metal, metal alloy, or composite.

13. The method according to claim 1, wherein said one or more 3-D tissue culture insert is round, square, triangular, rectangular, pentagonal, hexagonal, heptagonal, octagonal, nonagonal, or decagonal in shape.

14. The method according to claim 1, wherein said one or more 3-D tissue culture insert is removable or detachable from said tissue culture vessel.

15. The method according to claim 1, wherein said tissue culture vessel is provided on an apparatus, said apparatus comprising a programmable rocking platform or station that provides motion to said vessel to thereby generate hydrodynamic conditions to support 3-D cell aggregation.

16. The method according to claim 12, wherein said plastic is polystyrene, polypropylene, or polycarbonate.

* * * * *